US012653451B2

(12) United States Patent (10) Patent No.: US 12,653,451 B2
Canfield et al. (45) Date of Patent: Jun. 16, 2026

(54) HAIR ANALYSIS METHODS AND APPARATUSES

(71) Applicant: Canfield Scientific, Incorporated, Parsippany, NJ (US)

(72) Inventors: Douglas C. Canfield, Millburn, NJ (US); Mani V. Thomas, East Amwell, NJ (US); Zhen Lyu, Secaucus, NJ (US); Brian M. D'Alessandro, Chatham, NJ (US); Daniel E. DiGregorio, Fairfield, NJ (US)

(73) Assignee: Canfield Scientific, Incorporated, Parsippany, NJ (US)

( * ) Notice: Subject to any disclaimer, the term of this patent is extended or adjusted under 35 U.S.C. 154(b) by 972 days.

(21) Appl. No.: 16/896,849

(22) Filed: Jun. 9, 2020

(65) Prior Publication Data

US 2020/0383631 A1    Dec. 10, 2020

Related U.S. Application Data

(60) Provisional application No. 62/964,025, filed on Jan. 21, 2020, provisional application No. 62/859,130, filed on Jun. 9, 2019.

(51) Int. Cl.
*A61B 5/00* (2006.01)
*A61B 18/00* (2006.01)
(Continued)

(52) U.S. Cl.
CPC ............ *A61B 5/448* (2013.01); *A61B 5/0064* (2013.01); *A61B 5/446* (2013.01); *A61B 5/742* (2013.01);
(Continued)

(58) Field of Classification Search
None
See application file for complete search history.

(56) References Cited

U.S. PATENT DOCUMENTS 6,389,150 B1    5/2002  Amornsiripanitch
7,006,223 B2    2/2006  Mullani
(Continued)

FOREIGN PATENT DOCUMENTS

CN        108260918 B  *  5/2023  ............. A45D 44/00
EP         3479756 A1     5/2019
(Continued)

OTHER PUBLICATIONS

G. Maroni, V. Uberti, S. Facheris and F. Previdi, "A Computer Vision Algorithm for the Estimation of the Human Hair Diameter," 2018 IEEE 4th International Forum on Research and Technology for Society and Industry (RTSI), Palermo, Italy, 2018, pp. 1-6, doi: 10.1109/RTSI.2018.8548394. (Year: 2018).*
(Continued)

*Primary Examiner* — Matthew C Bella
*Assistant Examiner* — Johnny B Duong

(57) ABSTRACT

Methods and apparatuses are disclosed for capturing and analyzing images of human hair, particularly of a human scalp. Implementations described for capturing images at multiple locations on the scalp, detecting follicles and hairs, and generating a variety of measurements indicative of the condition of the hair, including the number and density of follicles, hair widths, inter-follicular distances, and the number of hairs per follicular unit, among other possibilities. Measurements can be compared among scalp locations, as well as among sequentially obtained images of the same location. A dermatoscope attachment for contact imaging of the scalp is also disclosed. The attachment may include polarizers enabling cross polarized imaging of the scalp.

20 Claims, 12 Drawing Sheets

(51) Int. Cl.

| | | |
|---|---|---|
| *G02B 27/28* | (2006.01) | |
| *G06T 7/00* | (2017.01) | |
| *G06T 7/13* | (2017.01) | |

(52) U.S. Cl.
CPC ............ *G02B 27/28* (2013.01); *G06T 7/0012* (2013.01); *G06T 7/13* (2017.01); *A61B 2018/00476* (2013.01); *G06T 2207/30088* (2013.01); *G06T 2207/30242* (2013.01)

(56) References Cited

U.S. PATENT DOCUMENTS

| | | | | |
|---|---|---|---|---|
| 7,986,987 | B2 * | 7/2011 | Bazin ..................... | A61B 5/441 |
| | | | | 600/478 |
| 9,167,999 | B2 * | 10/2015 | Zhang .................. | A61B 5/0077 |
| 10,573,026 | B2 * | 2/2020 | Kasprzak ............... | A61B 5/448 |
| 10,617,305 | B2 * | 4/2020 | Patwardhan ......... | A61B 5/0077 |
| 2003/0045799 | A1 | 3/2003 | Bazin et al. | |
| 2006/0178614 | A1 | 8/2006 | Nemati | |
| 2008/0216334 | A1 | 9/2008 | Pak et al. | |
| 2014/0243685 | A1 | 8/2014 | Patwardhan et al. | |
| 2014/0278321 | A1 | 9/2014 | Zhang et al. | |
| 2015/0036311 | A1 * | 2/2015 | Mullani ............... | A61B 5/0077 |
| | | | | 362/230 |
| 2022/0087596 | A1 * | 3/2022 | Marcu ..................... | G01J 3/021 |

FOREIGN PATENT DOCUMENTS

| | | | | | |
|---|---|---|---|---|---|
| KR | 101456942 | B1 * | 11/2013 | ............. | A61B 5/446 |
| WO | 2010036513 | A1 | 4/2010 | | |
| WO | WO-2015066618 | A1 * | 5/2015 | ......... | G06F 19/3481 |
| WO | 2017019437 | A1 | 2/2017 | | |
| WO | 2018017811 | A1 | 1/2018 | | |
| WO | 2018125218 | A1 | 7/2018 | | |

OTHER PUBLICATIONS

Cao, Yue, et al. "A Novel Method for Non-Destructive Determination of Hair Photo-Induced Damage Based on Multispectral Imaging Technology." Scientific Reports, vol. 7, No. 1, Mar. 2017, p. 45544. www.nature.com, https://doi.org/10.1038/srep45544. (Year: 2017).*

Benvenuto-Andrade, Cristiane, et al. "Differences Between Polarized Light Dermoscopy and Immersion Contact Dermoscopy for the Evaluation of Skin Lesions." Archives of Dermatology, vol. 143, No. 3, Mar. 2007, pp. 329-338. Silverchair, https://doi.org/10.1001/archderm.143.3.329. (Year: 2007).*

Hu, Ruiming, et al. "Trichoscopic Findings of Androgenetic Alopecia and Their Association with Disease Severity." The Journal of Dermatology, vol. 42, No. 6, Jun. 2015, pp. 602-607. DOI.org (Crossref), https://doi.org/10.1111/1346-8138.12857. (Year: 2015).*

Jain, Nilam, Bhavana Doshi, and Uday Khopkar. "Trichoscopy in alopecias: Diagnosis simplified." International journal of trichology 5.4 (2013): 170-178. (Year: 2013).*

Benvenuto-Andrade, Cristiane, et al. "Differences Between Polarized Light Dermoscopy and Immersion Contact Dermoscopy for the Evaluation of Skin Lesions." Archives of Dermatology, vol. 143, No. 3, Mar. 2007, pp. 329-338. Silverchair, https://doi.org/10.1001/archderm.143.3.329. (Year: 2018).*

Huang, Wen-Shiung, et al. "A cloud-based intelligent skin and scalp analysis system." 2018 IEEE Visual Communications and Image Processing (VCIP). IEEE, 2018. (Year: 2018).*

Su, Jian-Ping, et al. "An intelligent scalp inspection and diagnosis system for caring hairy scalp health." 2018 IEEE 7th Global Conference on Consumer Electronics (GCCE). IEEE, 2018. (Year: 2018).*

PCT/US2020/036797, Communication from the International Bureau re third party observations, PCT/IB/345, Jul. 9, 2021.

R. Hoffmann, Trichoscan: A Novel Tool for the Analysis of Hair Growth In Vivo, Soc. for Investigative Derm., 2003.

L. Rudnicka el al., Trichoscopy Report, Atlas of Trichoscopy, Springer-Verlag, 2012.

PCT/US2020/036797, Partial Search Result and Provisional Opinion of the International Searching Authority, Sep. 15, 2020.

PCT/US2020/036797, Final Search Result and Written Opinion of the International Searching Authority, Nov. 17, 2020.

M. Kasprzak et al., Follicular Map: A Novel Approach to Quantitative Trichoscopy, Skin Appendage Disord., Mar. 14, 2019.

EP Appl. No. 20750818.5, Communication pursuant to Rule 114(2) EPC, EPO, May 22, 2025.

EP Appl. No. 20750818.5, Communication pursuant to Article 94(3) EPC, EPO, Mar. 3, 2026.

* cited by examiner

*FIG. 4A*
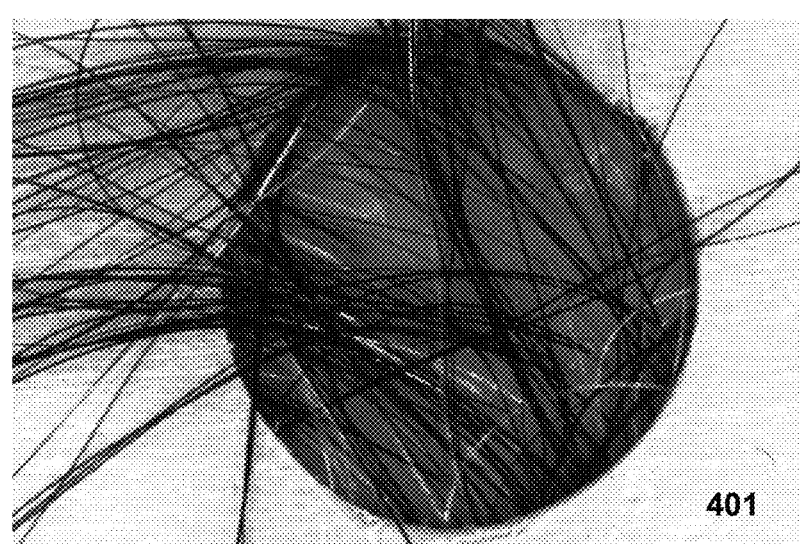
*FIG. 4B*
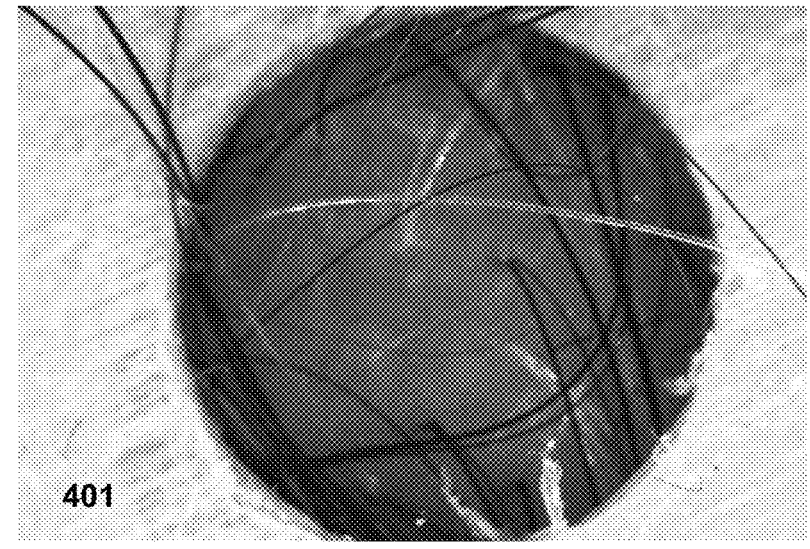
*FIG. 4C*

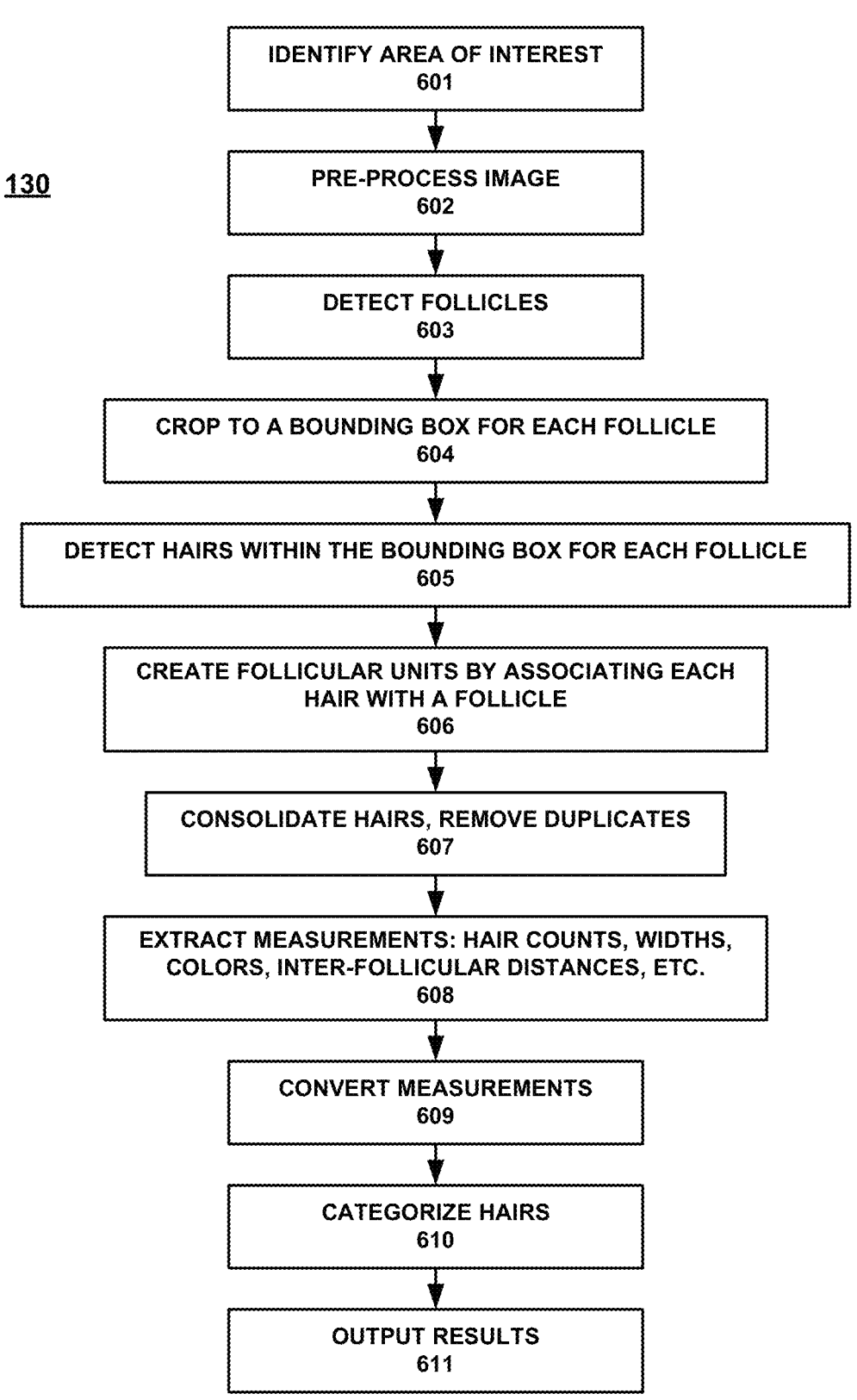

130

IDENTIFY AREA OF INTEREST
601

PRE-PROCESS IMAGE
602

DETECT FOLLICLES
603

CROP TO A BOUNDING BOX FOR EACH FOLLICLE
604

DETECT HAIRS WITHIN THE BOUNDING BOX FOR EACH FOLLICLE
605

CREATE FOLLICULAR UNITS BY ASSOCIATING EACH HAIR WITH A FOLLICLE
606

CONSOLIDATE HAIRS, REMOVE DUPLICATES
607

EXTRACT MEASUREMENTS: HAIR COUNTS, WIDTHS, COLORS, INTER-FOLLICULAR DISTANCES, ETC.
608

CONVERT MEASUREMENTS
609

CATEGORIZE HAIRS
610

OUTPUT RESULTS
611

HEAD

HAIR ANALYSIS METHODS AND APPARATUSES

RELATED APPLICATIONS

This Application claims priority from U.S. Provisional Patent Application No. 62/859,130, filed Jun. 9, 2019, and U.S. Provisional Patent Application No. 62/964,025, filed Jan. 21, 2020, both of which are incorporated herein by reference in their entireties.

FIELD OF THE APPLICATION

The present disclosure pertains to the capture and analysis of images of clipped and/or unclipped hair, such as hair on a human scalp, using a contact or non-contact imaging device.

BACKGROUND INFORMATION

There are a multitude of treatments, procedures, and products targeted to the health of hair, particularly head hair. Evaluating the merits of such offerings, however, has proven problematic, as such assessments are often subjective and qualitative. While there have been some efforts to provide more objective and quantitative assessment techniques, those available have shortcomings, such as being laborious, tedious, and often inaccurate.

SUMMARY OF THE DISCLOSURE

The present disclosure sets out apparatuses and methods for capturing images of hair, such as human head hair, analyzing the images of hair, and generating one or more measurements relating to the hair. More specifically, in one aspect the hair analysis apparatus is disclosed comprising a storage device containing instructions; and a processor for executing the instructions to obtain an image of an area of skin having hair; detect one or more follicles in the image; detect one or more hairs in the image; determine one or more measurements associated with the one or more follicles and the one or more hairs detected; and output a representation of the one or more measurements determined.

In another aspect, a hair analysis method is disclosed, the method comprising obtaining an image of an area of skin having hair; detecting one or more follicles in the image; detecting one or more hairs in the image; determining one or more measurements associated with the one or more follicles and the one or more hairs detected; and outputting a representation of the one or more measurements determined.

Additionally, a non-transitory computer-readable storage medium having stored thereon a computer program comprising instructions for causing a hair analysis apparatus to perform the foregoing method is also disclosed.

The present disclosure also sets forth an apparatus for use with a dermatoscope, comprising a contact plate, the contact plate having a shape corresponding to a hair clearance area to be imaged; and a body portion having a first end with a protrusion and a second end with a base, the protrusion having an opening for receiving the contact plate and the base being adapted to be removably attachable to the dermatoscope.

The aforementioned and other aspects of the present disclosure are set forth in greater detail below, with reference to the drawings filed herewith.

BRIEF DESCRIPTION OF THE DRAWINGS

FIGS. 4A through 4C are images of tools and their usage in preparing a clearance for imaging a scalp location in accordance with the present disclosure.

FIG. 6 is a flowchart of an exemplary image analysis procedure in accordance with the present disclosure.

FIG. 10 is a schematic representation of a dermatoscope with an attachment as used to image a scalp location in accordance with the present disclosure.

FIG. 11A is a plan view of the attachment of FIG. 10, whereas FIGS. 11B and 11C are elevation views thereof.

DETAILED DESCRIPTION

Figure 1:
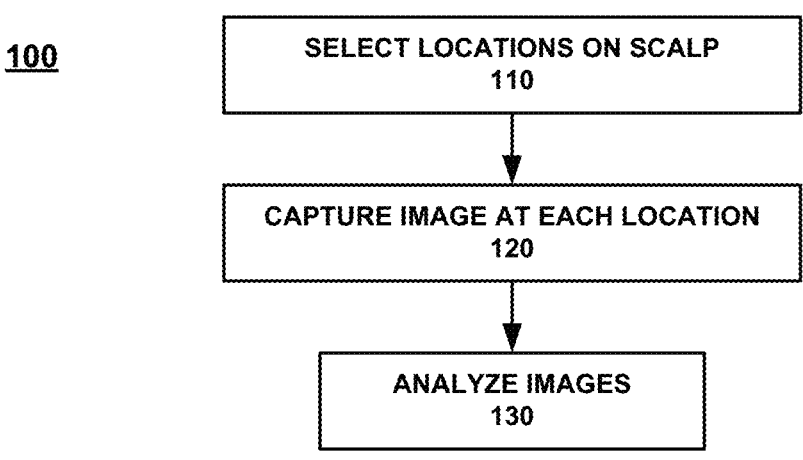
FIG. 1 is a high-level flowchart of an exemplary method in accordance with the present disclosure.

The following merely illustrates the principles of the present disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures, and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the disclosure.

In addition, it will be appreciated by those skilled in art that any flowcharts, process diagrams, and the like represent various processes which may be substantially represented in computer readable media and so executed by a computer or processor, whether or not such computer or processor is explicitly shown.

The functions of the various elements shown in the drawings, including any functional blocks, steps, procedures, modules, units or the like may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, dedicated circuitry, digital signal processor (DSP) hardware, network-based processors, application specific integrated circuitry (ASIC), read-only memory (ROM), random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown. Additionally, although illustrated as single elements, each such block or step shown may be implemented with multiple blocks or steps, or various combinations thereof. Terms such as "software," "application," "program," "firmware," or the like, are intended to refer, without limitation, to any instruction or set of instructions, structure, or logic embodied in any suitable machine-readable medium.

As used herein, the term "image" may encompass any form of photo-documentation, including 2D images and/or 3D surfaces and/or 3D volumetric image data, where a 2D image could be a single or a multichannel visible impression obtained by a camera, a 3D surface could be points in a 3D space connected by line segments to form a polygonal mesh along with any associated 2D images that represent the underlying texture, and 3D volumetric image data may represent a stack of 2D images that represent a 3D volume of the object being imaged.

Turning now to the drawings, FIG. 1 is a high-level flowchart of an exemplary method 100 in accordance with the present disclosure. In a first part 110, locations on the scalp of a subject are selected for imaging.

Figure 2:
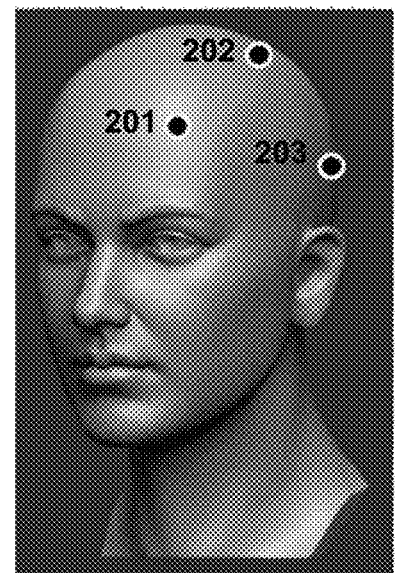
FIG. 2 is a representation of a human head indicating locations on the scalp to be imaged and analyzed in accordance with the present disclosure.

In exemplary implementations in accordance with the present disclosure, images of the scalp of a human head are obtained at multiple locations, such as those shown in FIG. 2. In the case of three locations, the preferred locations are at the temporal 201, vertex 202, and occipital 203 regions of the scalp, as shown in FIG. 2. Typically, hair transplantation involves moving hair from the occipital region 203 to the vertex 202 or temporal 201 regions of the scalp, since the occipital region is the region that is the least likely to lose hair. As for hair loss at the temporal 201 and vertex 202 regions, studies have indicated an ethnicity component, with Asian and Hispanic men, for example, having a greater propensity of losing hair in the vertex 202 and Caucasian men in the temporal 201 regions. Based on this assumption, various hair metrics, such as hair width, count, inter-follicular distances, and intensity, as described more fully below, are preferably computed with respect to the hair in the occipital region 203. As such, the occipital region 203 can serve as the control with differential metrics relative thereto being determined for the temporal 201 and vertex 202 regions.

Exemplary method 100 is readily adaptable to accommodate different numbers of images and locations and is not limited to those shown.

With the locations selected at 110, operation then proceeds to 120, in which one or more images are captured at each location. An exemplary procedure for doing so is described below in greater detail with reference to FIG. 3.

With the images captured at 120, operation proceeds to 130, in which the images are analyzed, including determining measurements associated with each image as well as differences in measurements associated with two or more images, such as measurements for the temporal and vertex regions relative to those of the occipital region. An exemplary procedure for doing so is described below in greater detail with reference to FIG. 6. Analysis may also include analysis of sequences of two or more images, so as to assess, for example, the efficacy of treatments applied between capture of the images. An exemplary procedure for such sequential analysis is described below in greater detail with reference to FIG. 9.

Figure 3:
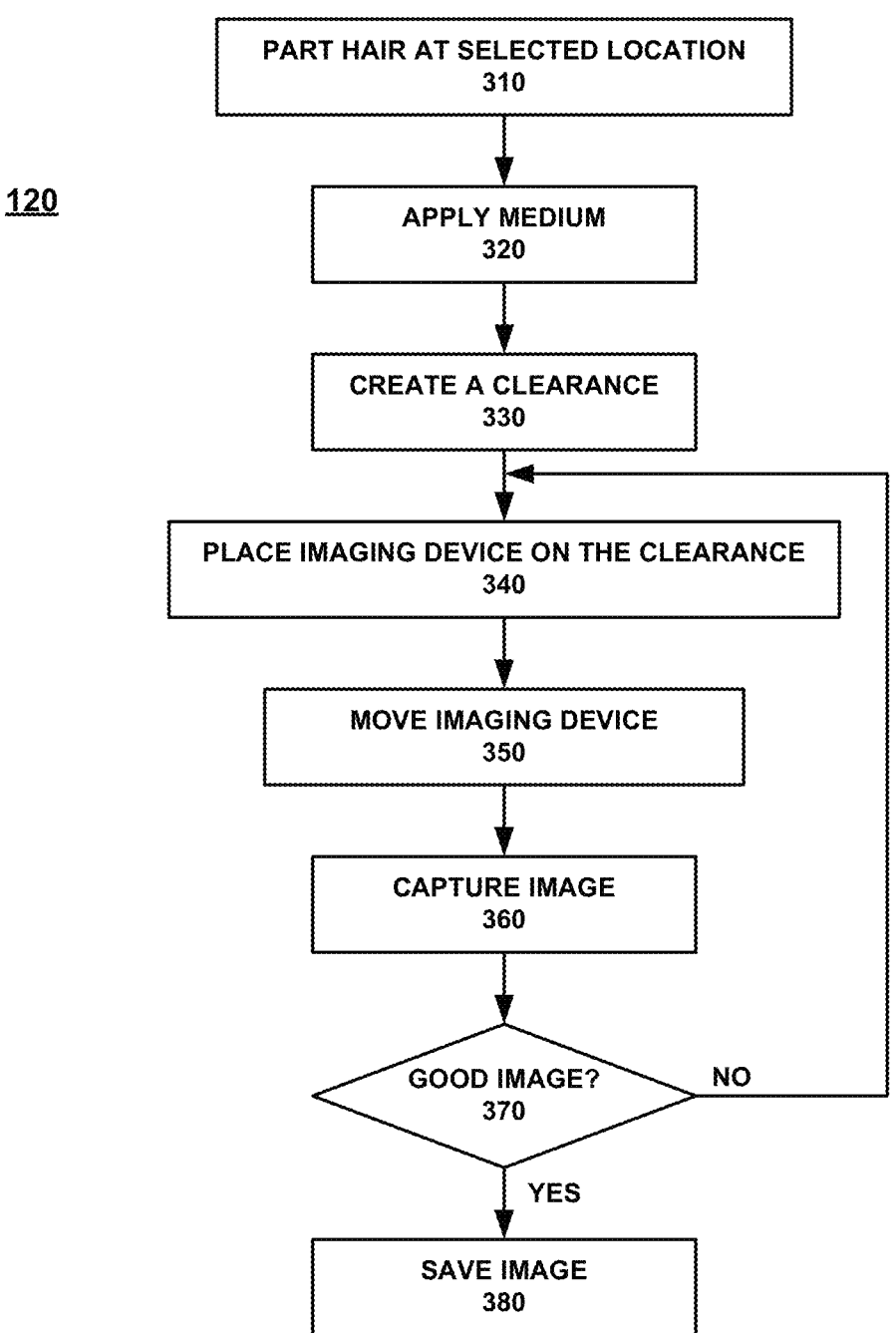
FIG. 3 is a flowchart of an exemplary image capture procedure in accordance with the present disclosure.

As mentioned, FIG. 3 schematically illustrates an exemplary image capture process in accordance with the present disclosure. In exemplary implementations, the image capture process depicted in FIG. 3 is carried out using a dermatoscope having image capturing capabilities such as the VISIOMED D200EVO ("D200") dermatoscope from Canfield Scientific, Inc. (https://www.canfieldsci.com/imaging-systems/visiomed-d200evo/). The D200 has the ability to capture images with 15× zoom up to 120× zoom, which makes it well suited for viewing and imaging skin lesions, among other things. In any case, the present disclosure is not limited to any particular imaging device or processing platform. In some embodiments, a mobile or portable device, such as a tablet computer with image capture capabilities can be used, possibly with optical enhancements for zoom imaging, with some or all of the processing as described below being carried out using the device.

We have found that cross-polarized filtering helps reduce specular reflection from the scalp and when used in tandem with a water-soluble gel reduces the observed skin flakes in the scalp. Standard white light images are not as helpful when trying to detect hair but can be used with a cross-polarized (Xpol) image to measure skin flakiness. Other imaging modalities are also possible and may be included in various implementations, described in greater detail below.

Before any images are captured at each of the locations 201-203, a hair parting operation 310 is carried out at each location, in which hair at the location to be imaged is manipulated to provide a clear image of the scalp. The hair can be parted with a comb or other suitable implement, preferably in the direction of hair growth.

Once the hair at the location selected for imaging has been parted, a light-conductive medium is applied at 320 to the area to be imaged. Preferably, a gel-like medium may be used, such as an ultrasound gel for example, to create a bond between the scalp and the contact plate of the imaging device. Otherwise, the presence of air between the contact plate and the skin will cause distortions. Such distortions can be eliminated or minimized by the use of a light-conductive gel having a refractive index that matches that of the contact plate, which is usually glass, or the like. Additionally, the medium is preferably water-soluble so that it can be easily removed from the hair once the procedure has been completed.

Substances other than ultrasound gel, such as isopropyl alcohol or hand sanitizer, for example, might be usable as the medium, but they may evaporate too quickly or be too runny. Also, in addition to serving as a good conductive medium between the contact plate and the scalp, a substance like ultrasound gel is also better suited in holding down the hair and maintaining the clearance. The adhesiveness of the gel helps part the hair and make a visibly strong clearance in the hair, or "runway." In any case, the amount of medium used is preferably minimized, so as to avoid image blur and the formation of air pockets.

It is also possible to additionally use fluorescence inducing agents and/or staining agents to capture multi-modal (e.g., XPol, UV, IR, etc.) images in quick succession. With the help of such agents, it may be possible to observe characteristics in the scalp (e.g., hair flakes, etc.), which when fused with other imaging modalities could be used to improve the accuracy of detection algorithms and/or the determination of other measurements such as the size and/or distribution of hair flakes, etc.

With the medium applied at 320, the comb and/or other hair management tools, such as those shown in FIG. 4A, are used at 330 to create a clearance in the scalp, or runway. As shown, such tools can include a loupe tool 401 and a hook tool 402. Loupe tool 401 can be implemented using a plastic (preferably a diffuse material) substrate that contains an opening, of any suitable shape, through which the hairs can be pushed aside using hook tool 402, which can be a crochet hook, for example, or any suitable hook-like tool that can be used to manipulate hair.

The exemplary loupe tool 401 shown in FIG. 4A has a circular opening, preferably with a standard diameter, such as 0.5 cm. The substrate can be of any color, but we have found from experiments that using a mostly "green" color maximizes color separation in a non-RGB (e.g., La*b*) color space, which in turn, helps to isolate the hair and scalp for analysis.

The process of using the loupe tool 401 involves placing it on the scalp and using the hook tool 402 to pull the hair aside, typically from below the loupe tool. The goal of this procedure is to clear the observable area of loose hair. FIG. 4B shows the tool applied to a location on the scalp before clearance. Once the area of interest is cleared, a contact or a non-contact imaging device is placed on or over the loupe tool 401 to capture an image such as that of FIG. 4C.

Another possible approach is to use a static gun to induce a static electric charge on the hair. Once the hair has been sufficiently charged, the movement of the hair can be controlled using a suitable plate with opposite polarity.

It should be noted that the use of tools such as the loupe 401 and hook 402 tools is one approach for creating a clearance or runway for imaging. A comb may suffice for this purpose. In addition, a dermatoscope with an attachment as described more fully below can be used advantageously. It should be also noted that the sequence of parting the hair at 310, then applying the medium at 320, followed by using the comb to part the hair some more at 330 may be an iterative process, which may need to be repeated for best results.

Referring again to FIG. 3, once the clearance or runway has been created at 330, operation proceeds to 340, in which the imaging device is placed over the clearance. If using the loupe tool 401, the FOV of the imaging device should be aligned with the opening of the loupe tool. At 350, the imaging device may need to be moved to optimize its position so as to obtain a good image that captures the entire clearance area even under high zoom levels. In moving the device, care should be taken not to upset the parted hair. Accordingly, in addition to finding the clearance upon initial placement of the device at 340 so as to minimize moving the device in search of the clearance, if movement at 350 is required it is preferable to move the device in line (parallel) with the runway. This was found to retain the parting reasonably well.

The size of the clearance area may depend on a variety of factors, such as the zoom level used, and hair length, as it is easier to part longer hairs and to maintain the clearance, with or without a loupe tool. In any case, to maximize the visible area, the field of view (FOV) of the imaging device is preferably matched to that of the area to be imaged, whether via the opening in the loupe tool or directly of a clearance area or runway created with a comb.

Figure 5B:
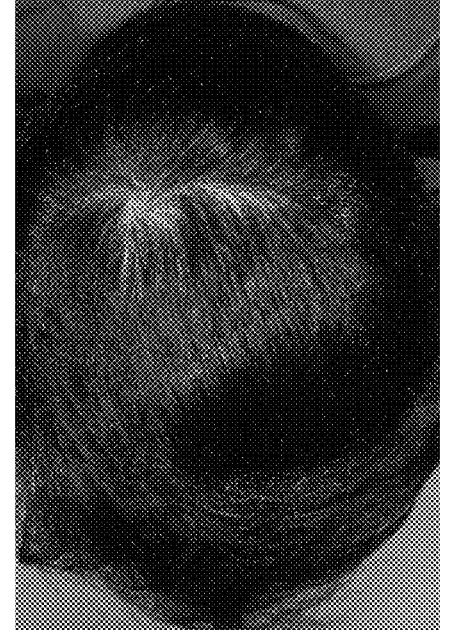
FIGS. 5A and 5B are images of illustrative head positioning devices suitable for imaging scalp locations in accordance with the present disclosure.
Figure 5A:

To assist with the placement of the imaging device, various arrangements can be employed, such as a stand with a chin cup to minimize movement of the subject's head, and/or a mechanical arm to hold the imaging device as it is moved into position, among other possibilities. Illustrative head positioning devices suitable for use with the D200 device, and possibly others, are shown in FIGS. 5A and 5B. Such devices allow the user to capture macro pictures of the subject and can be repurposed to stabilize the head to improve image capture.

Once the imaging device has been placed at 340 and moved, as needed, at 350, one or more images are captured at 360. The user can inspect the captured image at 370, and if unacceptable, can repeat the placement, movement, image capture and inspection steps 340-370, as needed. If at 370 the image is deemed satisfactory, it can be saved at 380 for further processing and analysis, as described below in greater detail.

Image capture procedure 120 is repeated for each of the locations 201-203 until one or more suitable images are captured for each of the locations. Once that has been completed, operation proceeds to 130, as indicated in FIG. 1, to analyze the captured images. An exemplary image analysis procedure 130 will now be described in greater detail with reference to FIG. 6.

Figure 7:
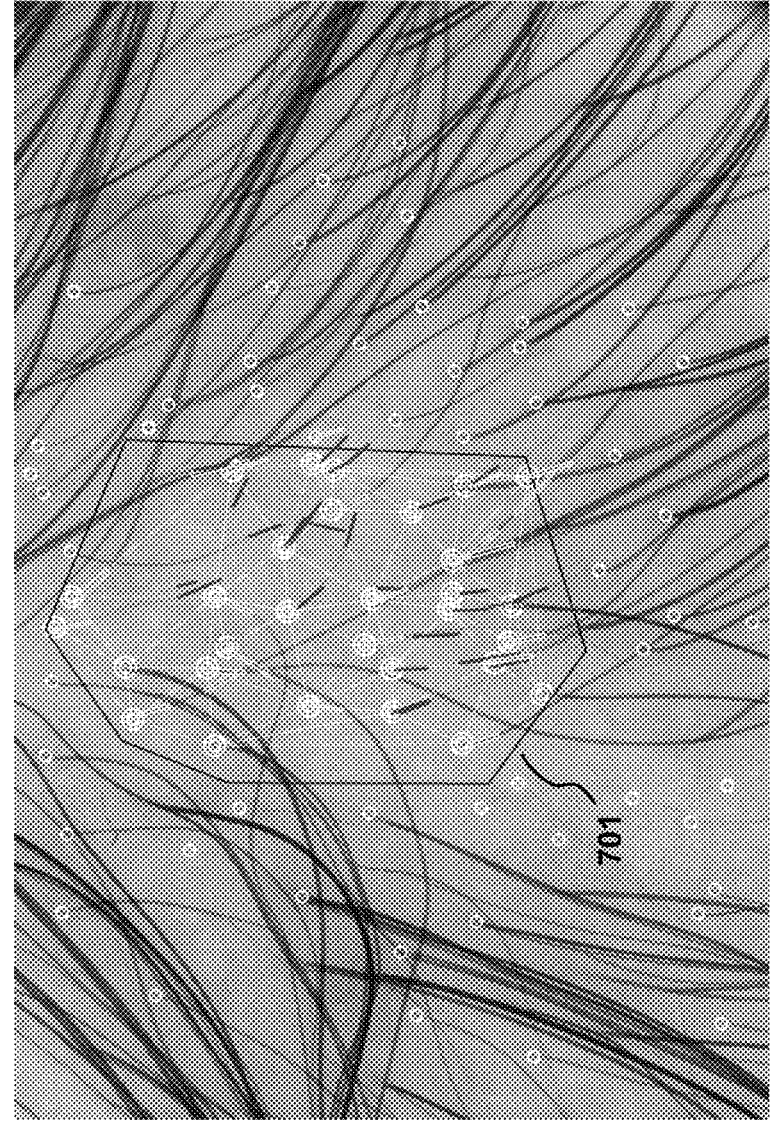
FIG. 7 is an image of a scalp location, with overlaid indicia for an area of interest (AOI), follicle locations, and hair widths, generated in accordance with the present disclosure.

In analyzing an image in accordance with the procedure of FIG. 6, operation begins at 601 with identifying an area of interest (AOI) in the image that includes the clearance or runway. The AOI can be specified either manually, with user input, or it can be automatically detected using a segmentation algorithm. The AOI may also be placed in a fixed location if an attachment which narrows the visible part of the scalp is used (as discussed later, and in FIG. 11). In an exemplary implementation, the image is presented to the user who could use an input device, such as a mouse, to mark the AOI in the image. An illustrative AOI 701 is shown in FIG. 7. As described more fully below, the analysis of the imaged hair is carried out using the AOI specified at 601.

At 602, the image can be pre-processed by performing one or more operations, such as increasing contrast and/or brightness, performing anisotropic diffusion, bilateral filtering, etc. (See, e.g., Joachim Weickert, "A Review of Nonlinear Diffusion Filtering", Scale-Space Theory in Computer Vision, Springer, LNCS 1252, July 1997, pp. 1-28.) The pre-processing can be limited to the AOI, or may be dispensed with, depending on the suitability of the contrast and brightness levels of the image as provided.

A follicle detection procedure is then performed at 603 to detect follicles at least within the AOI of the image being analyzed. This can be done, for example, using neural networks (e.g. deep learning), or traditional algorithms. Follicles can be identified by segmentation, bounding box, or both in combination. A detection neural network can be trained using an annotated data set. In the illustrative image of FIG. 7, the locations of the follicles detected are indicated by the small white circles.

Operation then proceeds to 604, in which a bounding box centered on each follicle is cropped out of the image. The size of each bounding box may be fixed or may vary depending on aspects of each follicle. Furthermore, only the pixels within a certain radius outside the follicle may be kept.

Operation then proceeds to 605 in which hairs within the bounding box of each of the detected follicles are detected. This can be done using one of several methods. In one implementation, individual hairs may be detected via a neural network (i.e., deep learning techniques, and/or convolutional neural networks). The neural network may be trained on an annotated ground truth data set, collected by manual, or semi-automatic methods. The output of the neural network on a given input image may be zero or more shapes, each representing an individual hair. In one embodiment, the shape is a rotated rectangle, specifying the center coordinate, length, width, and orientation of the hair. In other embodiments, the shape may be a polygon or one or more splines. A confidence metric, or probability that each detected shape is in fact a hair, may also be determined. The confidence metric, along with any other measurement on each hair, may be compared against one or more thresholds to filter out non-valid hairs.

Alternatively, at 605, individual hairs may be detected by conventional image analysis techniques, such as by computing a gradient-based image, curvilinear line analysis, or any other scale-space technique. This may include, for example, identifying curvilinear structures in the gradient image at one or more scales of the image, thus allowing the detection of curvilinear objects, ostensibly hair, of different widths.

Operation then proceeds to 606, in which each hair is associated with a follicle to construct a set of follicular units (follicles with their associated hairs). If hair detection occurs within bounding boxes centered around each follicle, then the hairs detected within a bounding box can be associated with the follicle of that bounding box. Alternatively, the hairs may be associated with follicles based on their proximity to the follicle centers.

Operation then proceeds to 607, in which the hairs across the image, at least in the area of interest, are evaluated to remove duplicate detections. This may be done, for example, using non-maximum suppression techniques using the confidence and location of each hair. So, for example, the overlap of two candidate hairs can be measured, and if the overlap exceeds a certain threshold value, the two can be considered to be the same hair.

Operation then proceeds to 608, in which the information from the operations at 603, 605, 606, and 607 is used to generate various desired measurements on the hairs, follicles, and/or follicular units. Measurements such as hair counts, hair widths, and hair colors, among others, may be computed or extracted from the preceding operations. These measurements may be computed on a global basis for the all detected follicles and hairs, or on a per-follicular unit basis.

The measurements may also include computed inter-follicular distances. In exemplary implementations, this can be done, for example, using a triangulation technique such as Delaunay triangulation to estimate optimal follicle interconnectivity, described below in greater detail. Alternatively, it may be possible to use a minimum spanning tree (MST) technique to measure the average distance.

Measurements may also include the color or intensity of each hair. In an exemplary implementation this can be done by identifying each isolated hair segment and computing the average color or intensity of the pixels representing the hair segment. The image pixels and resulting intensity values may be in any suitable color space, such as RGB, L*a*b*, or HSV, among others.

Operation then proceeds to 609 in which the measurements, based on pixels, are converted to absolute units using the image resolution (e.g., pixels per cm) of the images. Additionally, measurements, such as for example the numbers of follicles and hairs or the sum of hair widths, can be scaled, preferably to a unit square (e.g., of 1 cm$^2$ area, the standard typically used by practitioners). The scaled measurements at the temporal and vertex regions can then be compared with the corresponding measurements at the occipital region. The differences between the measurements at the vertex or temporal and the occipital regions give an estimate of hair loss.

Once the measurements have been converted at 609, operation proceeds to 610 to collect the measurements for each region and to categorize the hairs based on ranges of hair widths. For example, one possible set of hair width ranges is: (1)<30 μm, (2) 30 to 60 μm, (3) 60 to 90 μm, and (4)>90 μm. Hairs with widths in the first range, of less than 30 μm, are considered vellus or miniaturized hairs, whereas hairs with greater widths are considered terminal hairs.

Operation then proceeds to 611 to output the measurements and classifications determined above. The output can include displaying the image with an overlay of color-coded hairs. An illustrative such representation is shown in FIG. 7 with red indicating those hairs in the first, thinnest range of widths (<30 μm, i.e., vellus hair), yellow indicating those hairs in the second range (30-60 μm), dark green for hairs in the third range (60-90 μm), and light green for hairs in the fourth, or thickest range of widths (>90 μm). In addition, or as an alternative to such visual representations, the information can also be represented alphanumerically, graphically or in any other suitable form.

Figure 8:
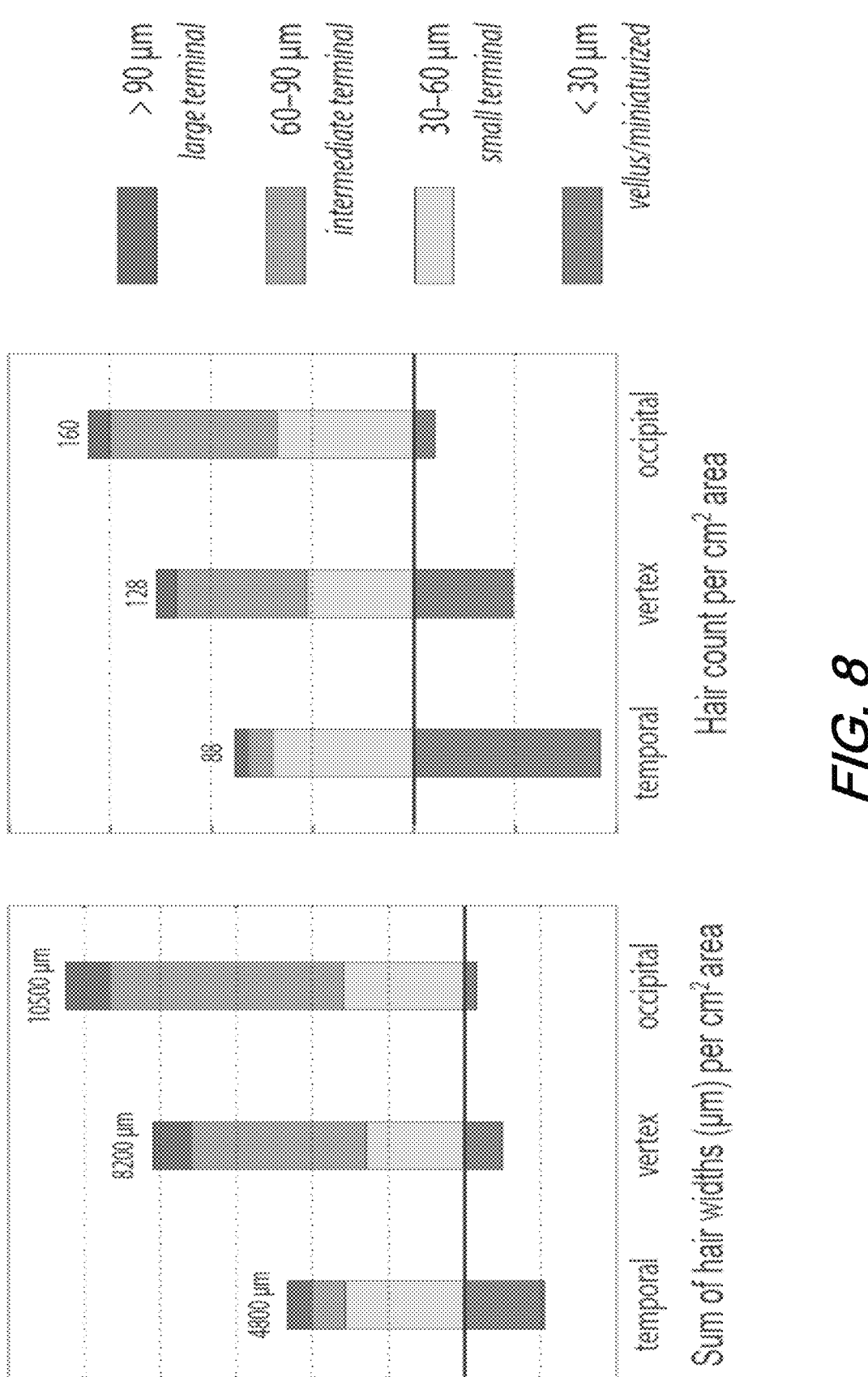
FIG. 8 shows illustrative stacked histograms of the sum of hair widths and hair counts per area for each of four ranges of hair widths at each of three scalp locations, generated in accordance with the present disclosure.

Information regarding the various categories of hair widths can be displayed, for example, using stacked histograms, such as those shown in FIG. 8, which show the sum of hair widths and hair count per cm$^2$ for each of the four ranges at each of the temporal, vertex and occipital locations. The hair width sums and counts for vellus hair are represented below the horizontal axis, readily distinguishable from the terminal hair measurements.

Other possible measurements that can be visualized include, without limitation, the sum of hair widths per cm$^2$; hair counts per cm$^2$; and/or the average intensity of the hair as a bar-graph from 0 to 1.0. These measurements may be computed for all hairs detected, or for one or more categories of hairs, such as terminal hairs, vellus hairs, small terminal hairs, intermediate terminal hairs, or large terminal hairs. The terminal hair count to vellus hair count ratio may be computed, as well as the average hairs per follicular unit, average hair width, follicle count per cm$^2$, average inter-follicular distance, and hair width diversity. Furthermore, while the determination of averages has been mentioned for parameters such as intensity and width, other suitable statistical metrics such as median, mode, and/or standard deviation, either with or without outlier removal may be determined as well or instead.

The output at 611 may also or alternatively include the display of inter-follicular distances obtained from the triangulation of follicles. This triangulation is shown in FIG. 7 as a white triangular mesh overlaid on the image of the scalp. Illustrative average values of this measurement are shown in the first column of TABLE 1 for the temporal, vertex and occipital regions imaged.

TABLE 1

|  | Inter-Follicular Distance (mm) | Number of Hairs per Follicular Unit | Number of Terminal Hairs per Follicular Unit |
|---|---|---|---|
| Temporal | 1.29 | 1.97 | 0.97 |
| Vertex | 1.46 | 2.52 | 1.83 |
| Occipital | 1.37 | 2.20 | 2.07 |

The measurement of the inter-follicular distance depends on the triangulation strategy employed. Typically, a standard Delaunay triangulation can be used but other methods are also possible (e.g., constrained Delaunay, conforming Delaunay, etc.; see, e.g., https://www.cs.cmu.edu/~quake/triangle.html).

Once the triangulation has been obtained, a mechanism to filter the edges/triangles should be used. This can be done using a variety of techniques. In one exemplary approach, this is done using a threshold on edge length. This entails iterating through all the edges and computing the average length of all the edges. Edges that are greater than twice the average length are removed. The remaining edges are used to calculate inter-follicular distance, such as by determining the average of their lengths.

In another exemplary approach, the ratio between the area of each triangle and the area of its circumcircle is used to filter the triangles. The largest value this ratio can take is $3 \times \sqrt{3}/4\pi = 0.4135$, which will be the case for an equilateral triangle. For any triangle that subtends the diameter of its circumcircle, the maximum ratio is $\sin(2\theta)/\pi$. For other triangles, this value will be smaller. This metric can be used to remove triangles that are very skinny, as those triangles will have very large circumcircles when compared to their areas. Another possible technique is to eliminate triangles whose largest angle exceeds a threshold value (e.g., 150 degrees) or whose smallest angle is less than a threshold value.

It should be noted that the exemplary method of FIG. 6 represents one possible implementation in accordance with the present disclosure. In other exemplary implementations, hairs could first be detected across the entire image, or at least the area of interest, and then later linked to follicles, without dealing with the cropping and bounding boxes, among other possibilities.

Another useful application of follicle and hair detection as described herein is the ability to track the locations of follicles and/or hairs over time in order to compare measurements. For example, one may wish to determine how the number of hairs per follicle has changed after undergoing a certain course of treatment. While there are methods to help capture a follow-up image in roughly the same location as the baseline capture, such as using identifying features on the scalp or a microdot tattoo, it is still difficult to exactly match the positioning. There will likely be small translation, rotation, or stretching differences between the two images due to how the camera was placed, the orientation of the photographer, the pressure of the capture device against the skin, etc. Such differences make it difficult to associate one individual follicle at baseline with that same follicle at a later timepoint. Without this association, automatically comparing measurements or data about individual hairs and/or follicles is not possible. Moreover, suitable identifying features such as nevi may not be present in the imaged area, and the application of a microdot tattoo may be undesirable, particularly in areas where the hair is sparse, in addition to being an additional procedure and causing some pain or discomfort to the subject.

Figure 9:
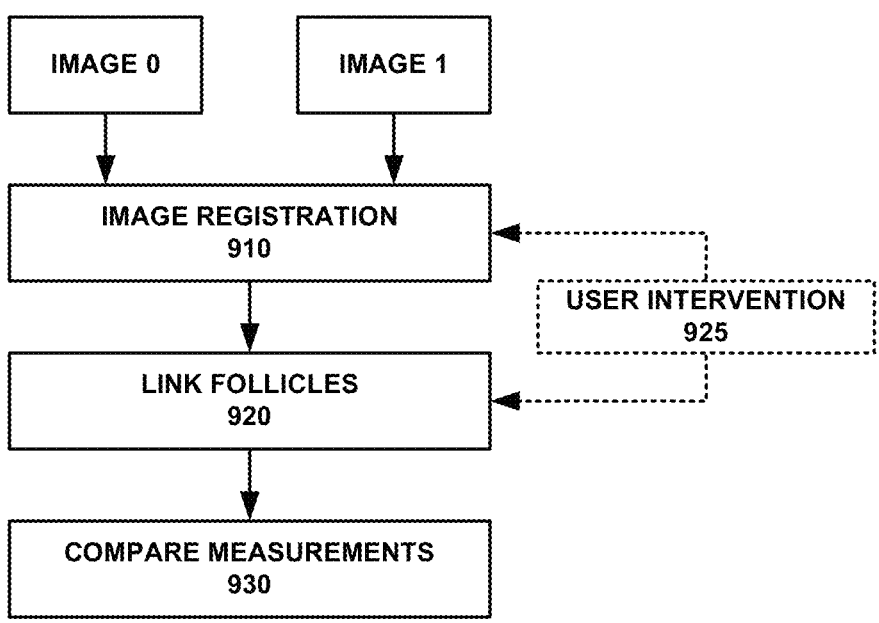
FIG. 9 is a flowchart of an exemplary procedure in accordance with the present disclosure for analyzing a sequence of two or more images of the same scalp location.

An exemplary procedure for analyzing two images, particularly of the same or proximate locations on the same scalp captured at different times, will now be described with reference to FIG. 9. To compensate for the positioning differences associated with the capture of the two images, such as those discussed above, the two images are subjected to an image registration algorithm at 910. A suitable registration algorithm that can be used at 910 is able to compare localized features in a first image (image 0) and in a follow-up image (image 1) to find common locations. Exemplary techniques that can be used for this purpose are described in U.S. Pat. No. 9,996,923 and U.S. Patent Application Publication No. 2019/0035080 A1, both of which are incorporated herein by reference in their entireties. Given these common locations, one image can be warped to match the other image. Alternatively, a vector field from the image registration, represented as a function $f(\ )$ can be used to map a pixel position $(x_0, y_0)$ in image 0 to the corresponding pixel position $(x_1, y_1)$ in image 1; i.e., $(x_1, y_1) = f(x_0, y_0)$. The inverse function may be used to likewise map from image 1 to image 0.

Given a dense correspondence between pixel locations in the images, as provided by the aforementioned registration techniques, a follicle detected in a first image may be tracked to the corresponding position in a second image. If a follicle was detected close to that position in the second image, the two follicles may be linked at 920 as being the same follicle, such as for example being associated with the same unique identifier. Due to small inaccuracies in tracking and/or follicle detection, however, the tracked position may not exactly line up. In that case, a nearest-neighbor search in the vicinity of the tracked position to find the closest follicle detected in the second image may be performed. If the closest follicle is within a distance d (e.g., ≤1.0 mm) to the tracked position, a determination can be made that the two follicles are the same. If not, a determination can be made that the follicle has disappeared. Likewise, by tracking in reverse, a determination can be made if a follicle has appeared.

Tracking and linkage of follicles may be assisted at 925 with user intervention, either by user input of key points to help the initial tracking algorithm, by fixing the overall orientation of the images, by providing known good key points that can assist with matching of neighboring points, or by fixing incorrect follicle matches.

Given one or more follicles that have been linked across two images, it is then possible at 930 to compare measurements about those follicles. For example, the number of hairs, width of hairs, length of hairs, color, or intensity of hairs coming out of the one or more follicles can be compared and a determination can be made if any of those measurements has changed. Such comparisons can be used, for example, to help evaluate the efficacy of treatment, or the effects of aging, disease, or other events or conditions that may have occurred or existed between the capture of the images.

While registration and tracking between two images has been described, these algorithms may also be applied to perform tracking over a series of images so as to bring correspondence and measurement comparison to an individual follicle in more than two images.

As discussed above, one imaging device that is well-suited for implementations in accordance with the present disclosure, is the D200 handheld dermatoscope. An attachment which further facilitates the use of this device to image the human scalp, will now be described with reference to FIGS. 10-13.

Figures 10, 11A, 11B, 11C:
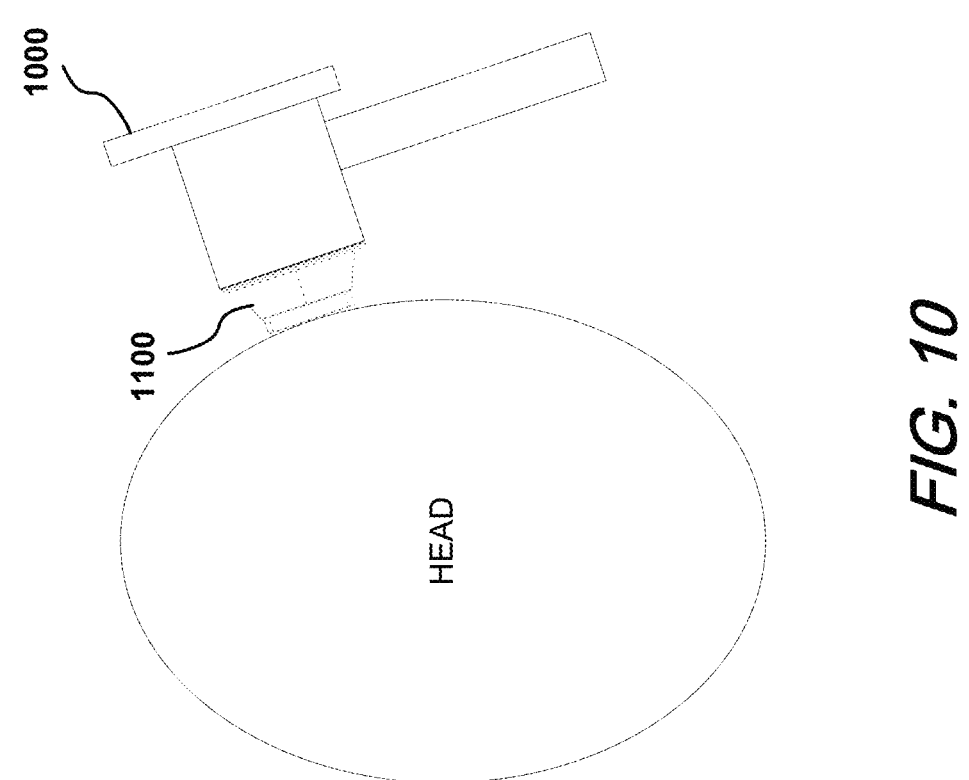
Figure 12:
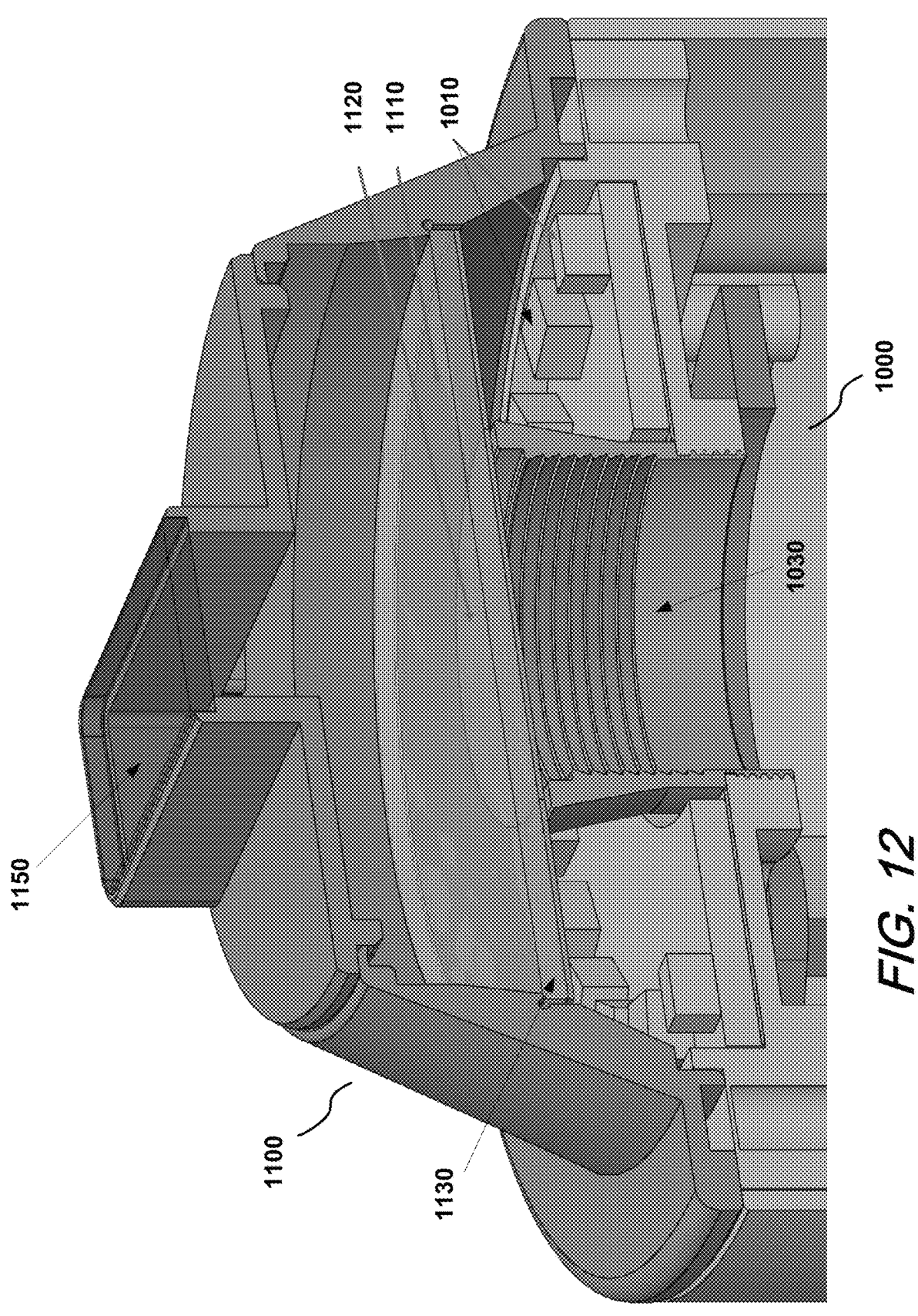
FIG. 12 is a first isometric cross-sectional view of the attachment attached to the dermatoscope.
Figure 13:
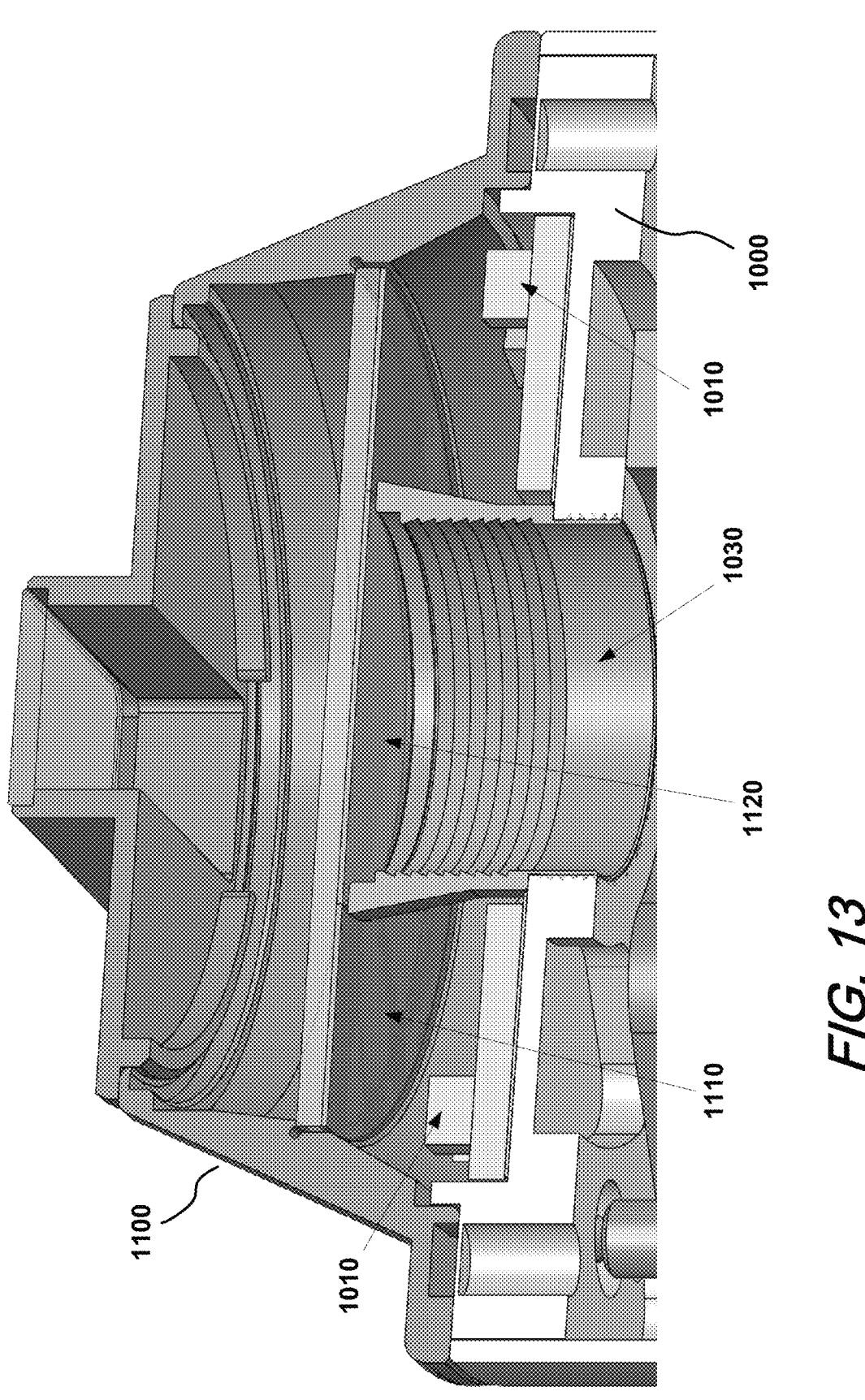
FIG. 13 is a second isometric cross-sectional view of the attachment attached to the dermatoscope.

As schematically depicted in FIG. 10, in operation in accordance with the present disclosure, handheld dermatoscope 1000 is held against the scalp as images are captured. Dermatoscope 1000 is fitted with an attachment 1100 that makes contact with the scalp. Attachment 1100, which generally has a frustoconical shape with a rectangular protrusion, is attached to the viewing opening of dermatoscope 1000. FIG. 11A is a plan view of attachment 1100, whereas FIGS. 11B and 11C are elevation views thereof. FIGS. 12 and 13 show two isometric cross-sectional views of the attachment 1100 attached to dermatoscope 1000. As can be appreciated from these figures, the round base of the attachment 1100 mates with the round viewing end of the dermatoscope, whereas the rectangular protrusion makes contact with the scalp at a location to be imaged.

More specifically, as shown in a cross-sectional isometric view in FIG. 12, the rectangular protrusion of attachment 1100 includes a contact plate 1150, which makes contact with the scalp, such as at a clearance or runway, to be imaged by dermatoscope 1000. Preferably, the contact plate 1150 is clear, with or without color filtering, and is made of a material (e.g., glass, plastic) with a refractive index close to that of the skin. The protrusion allows contact plate 1150 to contact the scalp, while providing clearance alongside the contact plate, such as for a tool, to remove or align hair so as to form a clearing or "runway" within the field of view of the contact plate.

As also shown in FIGS. 12 and 13, attachment 1100 may also include a first polarizer 1110 and a second polarizer 1120 arranged at an intermediate position between the round base opening and the rectangular protrusion. First polarizer 1110 is generally circular and is arranged in the viewing opening of the dermatoscope 1000 to polarize light entering via the contact plate 1150 and captured by the dermatoscope 1000 for imaging. Second polarizer 1120 is generally annular and surrounds first polarizer 1110 and acts to polarize light emitted from dermatoscope 1000, in particular, light emitted from light emitting devices 1010, such as light emitting diodes (LEDs) arranged concentrically around the viewing opening of the dermatoscope. In exemplary implementations, polarizers 1110 and 1120 are linear polarizers with mutually orthogonal polarization orientations. As shown, polarizers 1110 and 1120 are coplanar and are arranged between a clear backing plate 1130 of the attachment and a baffle 1030 in the viewing opening of the dermatoscope 1000. FIG. 13 shows an alternative isometric view of this arrangement from the side of dermatoscope 1000.

The provision of orthogonally oriented polarizing filters, such as polarizers 1110 and 1120 in attachment 1100, allow for the capture of cross-polarized images, which are well suited for imaging hair. As mentioned above, this imaging modality helps reduce specular reflection from the scalp, and when used in tandem with a light-conductive gel as described above reduces the observed skin flakes in the scalp.

Attachment 1100 is removably attachable to dermatoscope 1000 such as by a magnetic arrangement (e.g., a metallic ring at the base of the attachment and magnets in the mating surface of the dermatoscope), by an arrangement of mating threaded or interlocking surfaces, or other suitable mechanism.

It should be noted that the shape of an attachment in accordance with the present disclosure is not limited to that shown herein. For example, while exemplary attachment 1100 has a generally rectangular contact plate 1150 and a circular base, other shapes may be suitable, depending on the shape of the area to be imaged and the shape of the surface(s) of the dermatoscope to which the attachment is to mate. For example, a round or oval contact plate may be possible. Similarly, the shape in elevation of the protrusion can vary from that shown, so long as, preferably, it can accommodate access for tools to manipulate hair to clear the area to be imaged.

Advantageously, the methods and apparatuses disclosed herein can be used with both clipped as well as unclipped hair. Being able to obtain images with unclipped hair and to perform good quality analysis of such images is particularly desirable, as clipping hair may leave the subject with an undesirable void or discontinuity in their hair, which can take considerable time to grow back.

Figure 14:
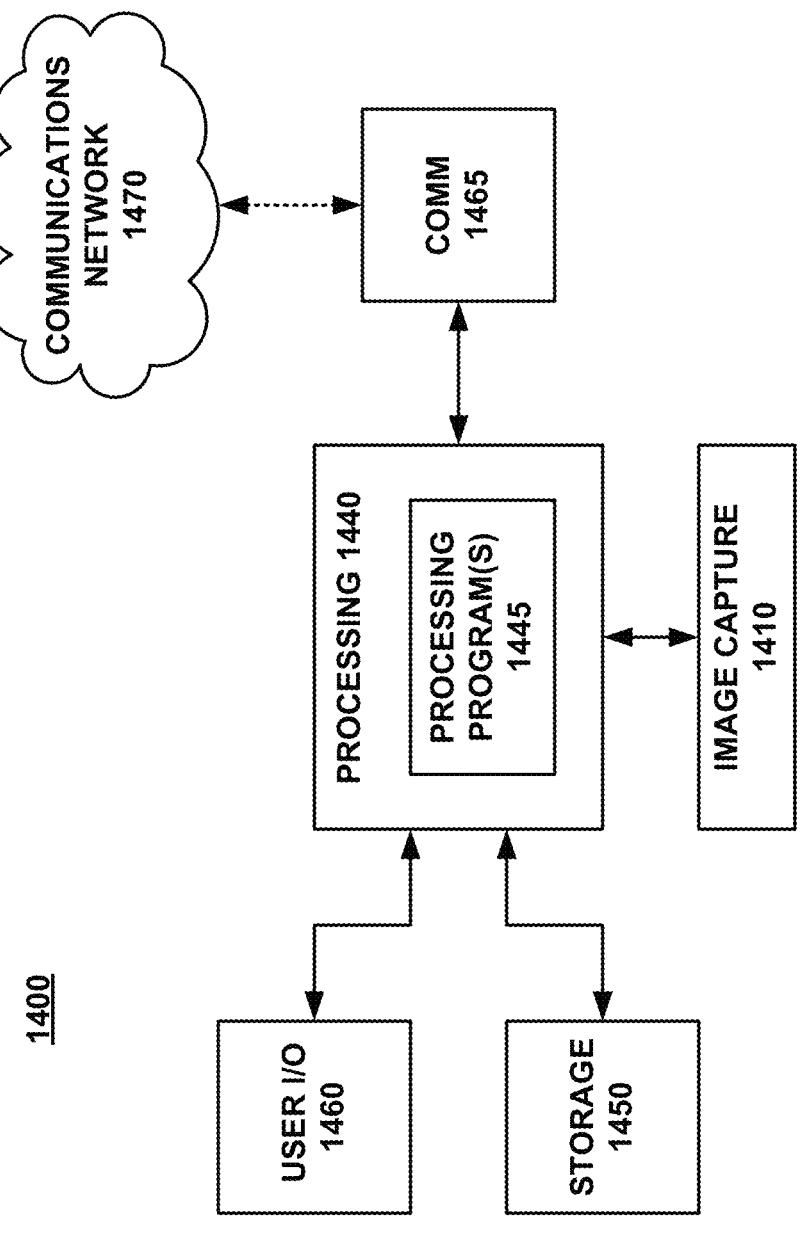
FIG. 14 is a schematic representation of an exemplary system in accordance with the present disclosure.

Turning now to FIG. 14, there is shown in schematic form an exemplary imaging system 1400 in accordance with the present disclosure. As shown in FIG. 14, components of system 1400 include an image capture system 1410 coupled to processing circuitry 1440. Image capture system 1410 may include one or more hand-held or mounted point-and-shoot or DSLR cameras, mobile cameras, frontal or rear-facing smart-device cameras, dermatoscopes (e.g., Canfield Scientific Inc.'s D200, VEOS devices), 2D skin imaging systems (e.g., Canfield Scientific Inc.'s VISIA), among others. Image capture system 1410 can be used to capture the various images described above.

Advantageously, the captured images can be single mode or multimodal—including, for example, those from standard white light, polarized light, and/or fluorescent light—captured at selected wavelengths and/or illuminated with selected wavelengths of light.

Images captured by image capture system 1410 are provided to processing circuitry 1440 for processing as described above. Of further advantage, processing circuitry 1440 may also control image capture system 1410, for example, by controlling one or more aspects of the image capture and/or illumination of the subject, such as exposure, modality, or filtering, among others.

Images may also be provided to processing circuitry 1440 from other sources and by other means. For example, images may be provided via communications network 1470, or in a non-transitory storage medium, such as storage 1450.

Processing circuitry 1440 may be coupled to storage 1450, for storing and retrieving images, among other data, and/or programs, software, and firmware, among other forms of processing instructions; and to input/output devices 1460, such as a display device and/or user input devices, such as a keyboard, mouse, touchscreen, or the like. Processing circuitry 1440 may also be coupled to a communications module 1465 for interconnection with a communications network 1470, such as a local network and/or the Internet, for transmitting and receiving images and/or data, and/or receiving commands, software updates or the like. Processing circuitry 1440, storage 1450, I/O 1460, and/or communications module 1465 may be implemented, for example, with one or more computers, workstations, processors, or the like, operating in accordance with one or more programs 1445 embodied in a compatible, non-transitory, machine-readable storage medium. Program(s) 1445 may be stored in storage 1450 and/or other memory devices (not shown), and provided therefrom and/or from communications network 1470, via communications module 1465, to processing circuitry 1440 for execution.

The various components of system 1400 may be connected via any suitable connection, including wired and/or wireless connections.

It should be noted that the exemplary system 1400 illustrates just one of a variety of possible arrangements contemplated by the present disclosure. For example, the various modules of system 1400 need not be co-located. For instance, image capture system 1410 and I/O devices 1460 can be located in a practitioner's office and processing circuitry 1440 and storage module 1450 can be remotely located, functioning within a telehealth framework, or be "cloud-based," interacting with image capture system 1410 and I/O devices 1460 over communications network 1470. In other exemplary arrangements, I/O devices 1460 can be remotely located from image capture system 1410, thereby allowing a user to remotely examine subjects' images. In other implementations, system 1400 can be implemented with a portable or mobile computing device, such as a tablet computer, smartphone, or the like.

Should this be primarily or particularly? We could use this to study any hair. Should we expand the wording here to include human scalp hair, hair in other parts of the body and animal hair?.

The foregoing merely illustrates principles of the present disclosure and it will thus be appreciated that those skilled in the art will be able to devise numerous alternative arrangements which, although not explicitly described herein, embody the principles of the disclosure and are within its spirit and scope. In addition, as can be appreciated, while specific implementations have been described above with respect to the analysis of human scalp hair, there are multiple applications entailing the analysis of images, whether of the same subject or multiple subjects, that could benefit from the techniques disclosed herein, including applications involving hair in other parts of human and/or animal bodies, among other possibilities.

Additionally, although illustrated as single elements, each block, step, or element shown may be implemented with multiple blocks, steps, or elements, or various combinations thereof. Also terms such as "software," "application," "program," "firmware," or the like, are intended to refer, without limitation, to any instruction or set of instructions, structure, or logic embodied in any suitable machine-readable medium. It is to be understood that numerous modifications may be made to the illustrative embodiments and that other arrangements may be devised without departing from the spirit and scope of the present disclosure.

At this point, while this disclosure has been presented using some specific examples, those skilled in the art will recognize that the teachings of this disclosure are not thus limited. The foregoing merely illustrates principles of the invention and it will thus be appreciated that those skilled in the art will be able to devise numerous alternative arrangements which, although not explicitly described herein, embody the principles of the invention and are within its spirit and scope. It is to be understood that numerous modifications may be made to the illustrative embodiments and that other arrangements may be devised without departing from the spirit and scope of the present invention as defined by the appended claims.

What is claimed:

1. A hair analysis apparatus comprising:
an image capture device configured to capture, through a contact plate, an image of an area of skin having hair, the hair being unclipped and parted in the area of skin and the contact plate having a shape that is generally rectangular or oval;
a storage device containing instructions; and
a processor configured to execute the instructions to:
detect one or more follicles in the image;
detect one or more individual hairs in the image;
determine one or more measurements associated with the one or more follicles and the one or more individual hairs detected; and
output a representation of the one or more measurements determined.

2. The apparatus of claim 1, wherein the representation includes one or more of an alphanumeric, graphical, or visual indication of the one or more measurements.

3. The apparatus of claim 1, wherein the processor is configured to execute instructions to:
obtain a further image, wherein the further image is of a further area of skin having hair, or of the area of skin captured at a time different than that at which the image was captured;
detect one or more follicles in the further image;
detect one or more individual hairs in the further image;
determine one or more further measurements associated with the one or more follicles and the one or more individual hairs detected in the further image; and
output a further representation of a difference between the one or more further measurements and the one or more measurements.

4. The apparatus of claim 3, wherein the processor is configured to execute instructions to determine a correspondence between follicles in the image and the further image.

5. The apparatus of claim 1, wherein the area of skin includes at least one of a temporal, vertex, or occipital area of a human scalp.

6. The apparatus of claim 1, wherein the one or more measurements include one or more of: a hair width, a number of hairs per follicular unit, an inter-follicular distance, a number of hairs per area, a number of follicles per area, a sum of hair widths per area, a hair color, a hair intensity, a ratio of terminal to vellus hair, a number of hairs per area of two or more width categories of hair, or a sum of hair widths per area of two or more width categories of hair.

7. The apparatus of claim 1, wherein the image is a plain white light reflectance image, an ultraviolet (UV) image, an infrared (IR) image or a cross-polarized image.

8. A method of a hair analysis apparatus, the method comprising:
capturing, through a contact plate, an image of an area of skin having hair, the hair being unclipped and parted in the area of skin and the contact plate having a shape that is generally rectangular or oval;
detecting one or more follicles in the image;
detecting one or more individual hairs in the image;
determining one or more measurements associated with the one or more follicles and the one or more individual hairs detected; and
outputting a representation of the one or more measurements determined.

9. The method of claim 8, wherein the representation includes one or more of an alphanumeric, graphical, or visual indication of the one or more measurements.

10. The method of claim 8 comprising:

obtaining a further image, wherein the further image is of a further area of skin having hair, or of the area of skin captured at a time different than that at which the image was captured;

detecting one or more follicles in the further image;

detecting one or more individual hairs in the further image;

determining one or more further measurements associated with the one or more follicles and the one or more individual hairs detected in the further image; and outputting a further representation of a difference between the one or more further measurements and the one or more measurements.

11. The method of claim 10 comprising determining a correspondence between follicles in the image and the further image.

12. The method of claim 8, wherein the area of skin includes at least one of a temporal, vertex, or occipital area of a human scalp.

13. The method of claim 8, wherein the one or more measurements include one or more of: a hair width, a number of hairs per follicular unit, an inter-follicular distance, a number of hairs per area, a number of follicles per area, a sum of hair widths per area, a hair color, a hair intensity, a ratio of terminal to vellus hair, a number of hairs per area of two or more width categories of hair, or a sum of hair widths per area of two or more width categories of hair.

14. The method of claim 8, wherein the image is a plain white light reflectance image, an ultraviolet (UV) image, an infrared (IR) image or a cross-polarized image.

15. The method of claim 8 comprising preparing the area of skin before capturing the image, including one or more of creating a clearance or applying a light conductive medium.

16. A non-transitory computer-readable storage medium having stored thereon a computer program comprising instructions for causing a hair analysis apparatus to perform the method of claim 8.

17. The apparatus of claim 1 comprising an attachment to the image capture device, the attachment including:

the contact plate; and a body portion having a first end with a protrusion and a second end with a base, the protrusion having an opening for receiving the contact plate and the base being adapted to be removably attachable to the image capture device.

18. The apparatus of claim 1, wherein the contact plate has an index of refraction matched to the skin.

19. The apparatus of claim 1 comprising:

a first polarizer for polarizing light captured by the image capture device; and a second polarizer for polarizing light emitted from the image capture device, wherein the first and second polarizers have polarizations with mutually orthogonal orientations.

20. The apparatus of claim 1, wherein detecting the one or more individual hairs is based on the one or more follicles detected.

\*   \*   \*   \*   \*